(12) United States Patent
Kelly et al.

(10) Patent No.: US 8,486,014 B2
(45) Date of Patent: Jul. 16, 2013

(54) SPIRAL PERFUSION DILATATION BALLOON FOR USE IN VALVULOPLASTY PROCEDURE

(75) Inventors: John Kelly, Galway (IE); Brian Kelly, Galway (IE); Herinaina Rabarimanantsoa-Jamous, Oranmore (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 149 days.

(21) Appl. No.: 13/072,689

(22) Filed: Mar. 26, 2011

(65) Prior Publication Data

US 2012/0245520 A1  Sep. 27, 2012

(51) Int. Cl.
*A61M 25/00* (2006.01)

(52) U.S. Cl.
USPC ............... 604/103.07; 604/96.01; 604/103.08

(58) Field of Classification Search
USPC ............... 604/96.01, 103.01, 103.08, 103.09, 604/914, 916; 606/194
See application file for complete search history.

(56) References Cited

U.S. PATENT DOCUMENTS

| | | | |
|---|---|---|---|
| 5,181,911 A | 1/1993 | Shturman | |
| 5,226,888 A * | 7/1993 | Arney | 604/103.07 |
| 5,649,978 A | 7/1997 | Samson | |
| 6,478,778 B1 | 11/2002 | Jacobsen et al. | |
| 7,951,111 B2 * | 5/2011 | Drasler et al. | 604/103.13 |
| 2003/0120208 A1 * | 6/2003 | Houser et al. | 604/103.04 |

* cited by examiner

*Primary Examiner* — Laura Bouchelle

(57) ABSTRACT

A balloon dilatation catheter for use in a valvuloplasty procedure includes a catheter shaft and a spiral perfusion balloon mounted thereon. The perfusion balloon is formed from an inflatable tube that is in fluid communication with a catheter shaft inflation lumen. The inflatable tube is coiled into a series of windings that in an inflated configuration form a cylindrical or hourglass profile. In the inflated configuration, inner surfaces of the coiled windings of the inflatable tube define a perfusion lumen to allow blood flow through the perfusion balloon. Adjacent windings may be secured together with a flexible adhesive and/or a support weave formed from one or more filaments of material that criss-crosses between the adjacent windings along substantially the entire length of the spiral perfusion balloon.

11 Claims, 7 Drawing Sheets

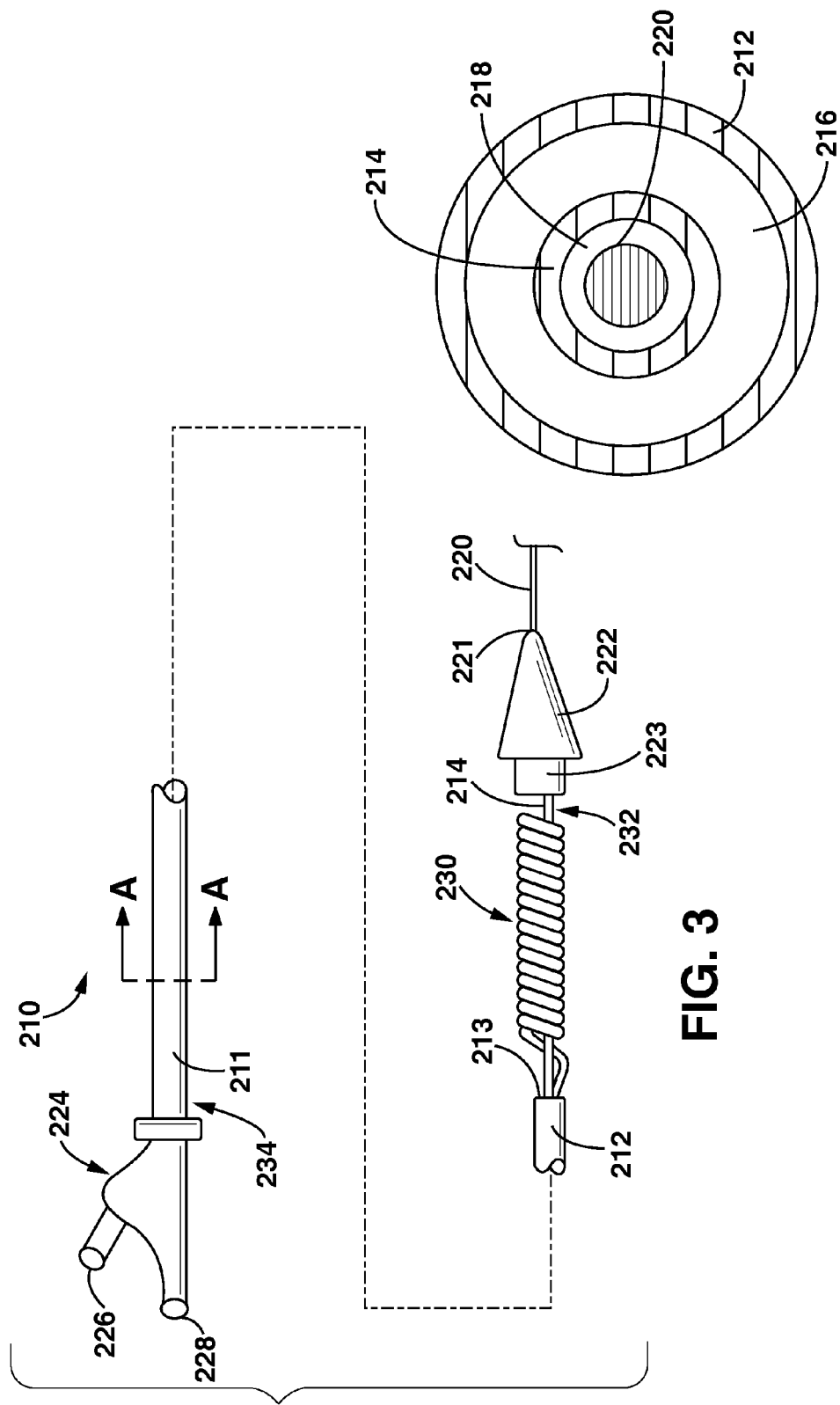

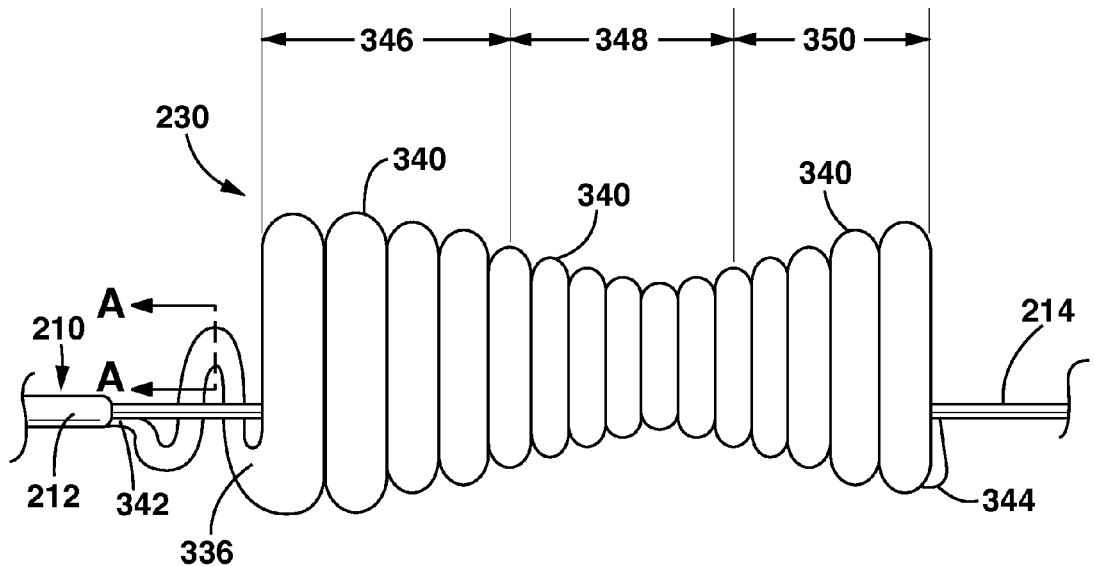
FIG. 5
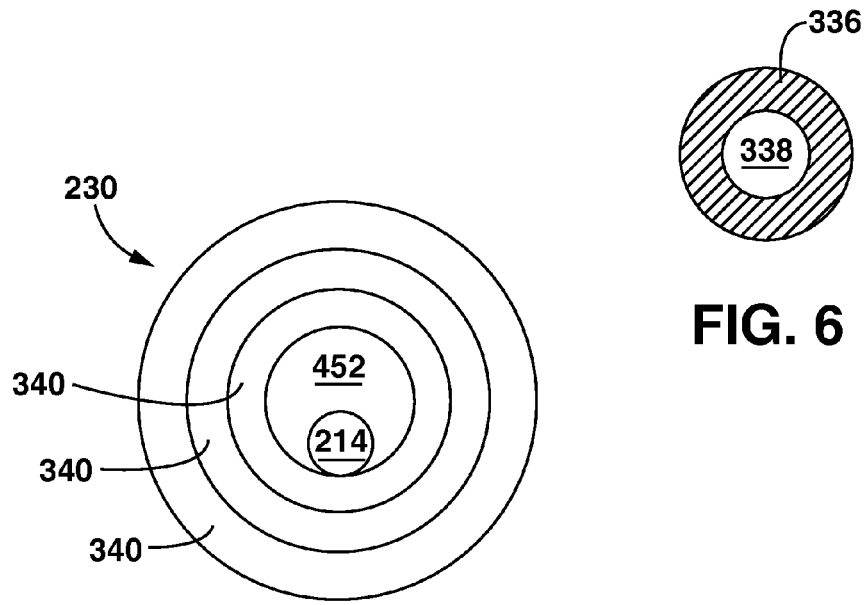
FIG. 6
FIG. 7

SPIRAL PERFUSION DILATATION BALLOON FOR USE IN VALVULOPLASTY PROCEDURE

FIELD OF THE INVENTION

The invention relates to a spiral perfusion balloon for use in a valvuloplasty procedure.

BACKGROUND OF THE INVENTION

Heart valves, such as the mitral valve, tricuspid, aortic and pulmonic valves, are sometimes damaged by disease or by aging, which can interfere with the proper functioning of the valve. Heart valve problems generally take one of two forms: stenosis, in which a valve does not open completely such that the opening is too small, resulting in restricted blood flow; or insufficiency, in which a valve does not close completely, permitting blood to leak backward across a valve that should be closed. The most common form of heart valve disease is aortic stenosis where the aortic valve leaflets become calcified and stiff, reducing the functioning valve area. The underlying disease state may be congenital or acquired. Valve replacement may be required in severe cases to restore cardiac function. The native aortic valve is removed and replaced with a prosthetic valve, or a prosthetic valve is placed within the native valve. The valve replacement may be a mechanical or biological valve prosthesis.

Another treatment approach for aortic stenosis is aortic valvuloplasty, also referred to as balloon valvotomy. During valvuloplasty, a dilating balloon is inflated to help crack the calcification on the valve leaflets allowing them to move more freely. This may be a stand-alone treatment giving a patient improved valve function for 6 to 12 months, or it may be a conjunctive treatment, preparing the valve before a valve implant. As shown in FIG. 1, aortic valvuloplasty includes positioning an unexpanded balloon 108 of a balloon catheter 106 across the aortic valve 100 so that balloon 108 spans valve 100 with one end of balloon 108 being located in the aorta 102 and the other end of balloon 108 being located in the left ventricle 104. Once thus positioned, balloon 108 is inflated to dilate the patient's aortic valve as shown in FIG. 2, thereby relieving the stenosis. Since blood flow through the valve is often blocked during the procedure, correct placement of the balloon may be facilitated by accelerating the heart rate with an external pacemaker to reduce cardiac output and ventricular pressure.

The present disclosure is directed to a balloon for use in valvuloplasty that allows for perfusion during the procedure and that may be more readily secured and centered at the treatment site.

BRIEF SUMMARY OF THE INVENTION

Embodiments hereof relate to a spiral perfusion dilatation balloon for use in a valvuloplasty procedure. The spiral perfusion balloon includes an inflatable tube having an inflation lumen extending therethrough. The tube is wound about a central axis to create a series of flanking coils having inner surfaces that define a perfusion lumen of the perfusion balloon to allow blood flow therethrough. When inflated, the coiled tube forms an hourglass profile having an intermediate section disposed between proximal and distal sections. At least one winding of the intermediate section has a reduced outer diameter relative to an outer diameter of at least one winding in each of the proximal and distal sections. When deflated, the coiled tube is collapsed to a low profile.

According to another embodiment hereof, a balloon catheter for use in a valvuloplasty procedure includes a catheter shaft having an inflation lumen. A spiral perfusion dilatation balloon is mounted about a distal portion of the catheter. The spiral perfusion balloon is formed from an inflatable tube having a balloon inflation lumen extending therethrough and being in fluid communication with the catheter inflation lumen. The tube is wound about a central axis to create a series of flanking coils having inner surfaces that define a perfusion lumen of the perfusion balloon to allow blood flow therethrough. When inflated, the coiled tube forms an hourglass profile having an intermediate section disposed between proximal and distal sections. At least one winding of the intermediate section has a reduced outer diameter relative to an outer diameter of at least one winding in each of the proximal and distal sections. When deflated, the coiled tube is collapsed to a low profile.

According to another embodiment hereof, a spiral perfusion dilatation balloon for use in a valvuloplasty procedure includes an inflatable tube having an inflation lumen extending therethrough. The tube is wound about a central axis to create, in an inflated configuration a series of flanking coils having inner surfaces that define a perfusion lumen of the perfusion balloon to allow blood flow therethrough. The adjacent windings of the inflatable tube are secured to each other with a support weave formed from one or more filaments that are woven between adjacent windings along substantially the entire length of the balloon.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 3 is a broken side view of a catheter having a spiral perfusion dilatation balloon at the distal end thereof, wherein the spiral perfusion balloon is in an unexpanded configuration, in accordance with an embodiment hereof.

FIG. 4 is a transverse cross-sectional view of the catheter of FIG. 3 taken along line A-A.

FIG. 5 is an enlarged side view of a distal portion of the catheter of FIG. 3, wherein the spiral perfusion balloon is in an expanded configuration.

FIG. 6 is a transverse cross-sectional view of a spiraling tube of the balloon catheter of FIG. 5 taken along line A-A.

FIG. 7 is a distal end view of the balloon catheter of FIG. 5, with the distal tip of the catheter removed for clarity.

DETAILED DESCRIPTION OF THE INVENTION

Figure 2:
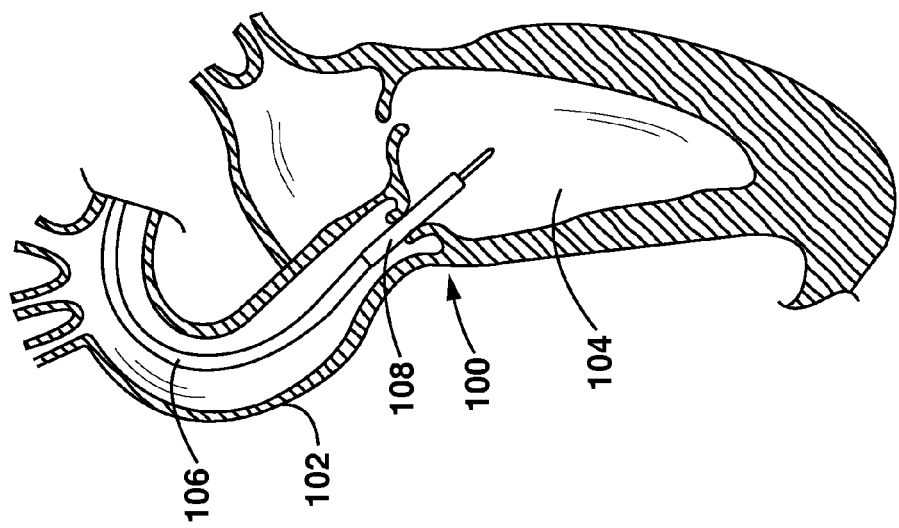
FIGS. 1 and 2 are schematic representations of a known aortic valvuloplasty procedure.
Figure 1:
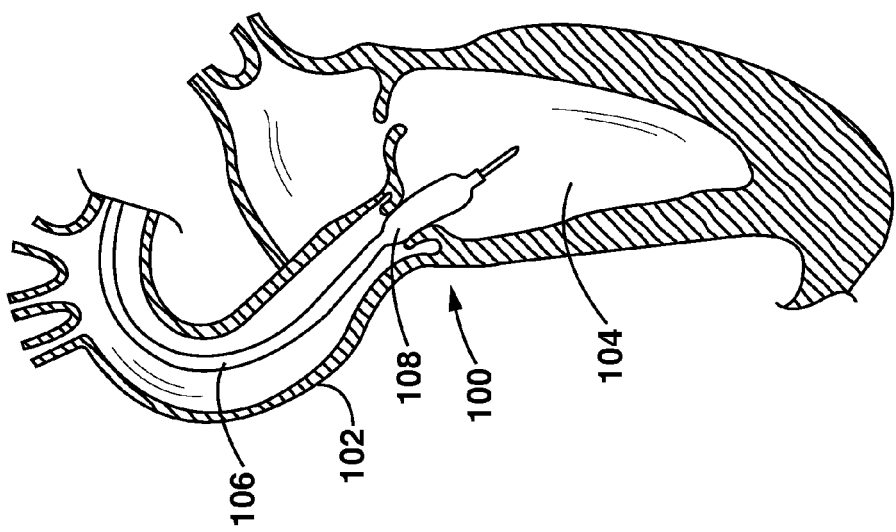

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

The following detailed description is merely exemplary in nature and is not intended to limit the invention or the application and uses of the invention. Although the description of the invention is in the context of treatment of heart valves, such as the mitral, tricuspid, aortic and pulmonic valves, the invention may also be used in any other body passageways where it is deemed useful. Furthermore, there is no intention to be bound by any expressed or implied theory presented in the preceding technical field, background, brief summary or the following detailed description.

FIGS. 3-7 depict a dilatation balloon catheter 210 for use in a valvuloplasty procedure according to an embodiment hereof. Balloon catheter 210 includes an inflatable spiral perfusion dilatation balloon 230 that is positionable at a target location within the vasculature. Balloon 230 is shown in an unexpanded, deflated or delivery configuration in FIG. 3 and in an expanded or inflated configuration in FIGS. 5-7. A retractable delivery sleeve (not shown) may be slid over spiral perfusion balloon 230 to minimize the profile of the balloon in the deflated configuration as well as to protect the balloon during navigation of balloon catheter 210 through a patient's vasculature.

In the illustrated embodiment, balloon catheter 210 has coaxial over-the-wire (OTW) catheter construction and includes an elongate catheter shaft 211. Although balloon catheter 210 is shown in this embodiment in an over-the-wire configuration, those of ordinary skill in the art would recognize that other catheter configurations known in the art, such as side-by-side lumen configurations or rapid exchange configurations, may also be suitable. More particularly, elongate catheter shaft 211 includes a tubular inner shaft 214 that extends coaxially within a tubular outer shaft 212 such that an annular inflation lumen 216 is defined between an inner surface of outer shaft 212 and an outer surface of inner shaft 214. A distal end 232 of elongate catheter shaft 211 may be attached to a tapered, ogival or otherwise rounded distal tip 222 to assist in navigation of balloon catheter 210 through a patient's vasculature. As shown, distal tip 222 is shaped to include a reduced diameter proximal step 223 that is sized to be received within a distal end of a retractable delivery sheath (not shown). A proximal end 234 of elongate catheter shaft 211 extends out of the patient and is attached to a fitting or manifold 224.

As explained in more detail below, spiral perfusion dilatation balloon 230 is mounted over a distal segment of inner shaft 214 and is in fluid communication with inflation lumen 216, which allows inflation fluid received through an inflation port 226 of manifold 224 to be delivered to balloon 230. As would be understood by one of ordinary skill in the art of balloon catheter design, manifold 224 provides a luer hub or other type of fitting that may be connected to a source of inflation fluid and may be of another construction or configuration without departing from the scope of the present invention.

Inner shaft 214 extends through the entire length of outer shaft 212 and defines therewithin a guidewire lumen 218 extending substantially the entire length of the catheter for accommodating a guidewire 220. A proximal end of inner shaft 214 is coupled to a guidewire port 228 of manifold 224, and a distal end of inner shaft 214 terminates distally of balloon 230 and defines a distal guidewire port 221 that allows balloon catheter 210 to be tracked through the vasculature over guidewire 220.

Outer and inner shafts 212, 214 may be formed of any suitable flexible polymeric material. Non-exhaustive examples of material that may be used for the catheter shafts are polyamide, polyurethane, polyethylene, polyethylene block amide copolymer, or combinations of any of these materials, either blended or layered or sequentially joined. Optionally, a portion of the outer shaft 212 may be formed as a composite having a reinforcement material incorporated within a polymeric body to enhance physical properties such as compression strength and kink resistance. Suitable reinforcement layers may include wrapped mesh or filaments that are braided, helically wrapped, or laid axially as warp filaments, as would be known to one of skill in the art of catheter construction. Catheter shaft 211 may have any suitable working length, for example, 90-110 cm, to extend from an entry site such as, for example only, a femoral artery to a target location where the spiral perfusion balloon 230 is to be inflated. Other types of catheter construction are also amenable to the present invention, such as, without limitation thereto, a catheter shaft formed by a multi-lumen extrusion or in a rapid exchange configuration.

In FIGS. 5-7, spiral perfusion dilatation balloon 230 is illustrated in its inflated or deployed configuration. Spiral perfusion balloon 230 is formed from an inflatable tube 336 coiled in a helical fashion around a central axis into a series of windings or loops 340, with consecutive or adjacent turns or windings 340 stacked against and contacting each other with substantially no space therebetween. As illustrated in FIG. 7, an inner surface of spiral perfusion balloon 230 defines a perfusion lumen 452 through the open center of the helix when spiral perfusion balloon 230 is inflated. By allowing blood to flow through perfusion lumen 452 during dilation of a valve, spiral perfusion balloon 230 reduces blood pressure that would otherwise build up and tend to eject the balloon from within the valve. Thus, a perfusion valvuloplasty balloon may allow for longer periods of balloon inflation and dilation of the valve for improved procedural outcomes. In addition, the heart may not need to be put into rapid pacing during a valvuloplasty procedure performed with a spiral perfusion balloon since at least some blood continues to flow through the heart during dilation of the valve.

Inflatable tube 336 of spiral perfusion balloon 230 extends from proximal end 342, which is also the proximal end of spiral perfusion balloon 230, to a closed or capped distal end 344, which is also the distal end of spiral perfusion balloon 230. A fluid passageway or balloon inflation lumen 338 extends substantially the full length of tube 336. In one embodiment, connection between spiral perfusion balloon 230 and elongate catheter shaft 211 is at least partially provided by skiving an opening into the distal end 213 of outer shaft 212, inserting tube proximal end 342 of therein such that balloon inflation lumen 338 is in fluid communication with catheter shaft inflation lumen 216. The assembly may then be heat bonded to form a secure fluid-tight connection between tube 336 and shaft 211. Inflation fluid delivered through catheter shaft inflation lumen 216 thus serves to inflate spiral perfusion balloon 230. In various embodiments, inflatable tube 336 may have an outer diameter of approximately 5 mm and a wall thickness in the range of 0.001 to 0.002 inches. Inflatable tube 336 may be made of a polymeric material such as may commonly be used for dilatation balloons, including without limitation polyethylene terephthalate (PET), polyamide 12 or polyethylene block amide copolymer. When balloon 230 is deflated, tube 336 may collapse or flatten, thus assisting the overall spiral structure of balloon 230 to collapse into a low profile configuration, which may comprise one or more folds or wings that wrap around the distal segment of inner shaft 214 as would be understood by those familiar with cylindrical, non-helical dilatation balloons.

As shown in FIG. 5, inflated spiral perfusion dilatation balloon 230 has three integral portions or sections including a proximal section 346, a distal section 350, and an intermediate or waist section 348 disposed therebetween. At least one of windings 340 in waist section 348 has a smaller outer diameter than at least one of windings 340 in each of proximal and distal sections 346, 350 such that spiral perfusion balloon 230 has a generally hourglass-shaped profile. Stated another way, the outer diameters of windings 340 are varied along the length of inflated spiral perfusion balloon 230 to form a perfusion balloon with an hourglass shape. The hourglass profile aids in the positioning of spiral perfusion balloon 230 during the procedure because waist section 348 tends to axially center spiral perfusion balloon 230 within the aortic valve. In addition to centering the balloon during the procedure, the hourglass profile may secure spiral perfusion balloon 230 within the aortic valve because inflated proximal section 346 may lodge against the aortic wall. In various embodiments, one or more of the windings of proximal and distal sections 346, 350 may have a maximum outer diameter in the range of 26-32 mm and one or more of the windings of waist section 348 may have a minimum outer diameter in the range of 16-24 mm. For purposes of comparison only, the average diameter of the aortic valve in an adult human has been reported to be at least 20 mm. In one embodiment, the reduced outer diameter of one or more windings of waist section 348 is between 75% and 95% of the outer diameter of one or more windings in each of the proximal and distal sections 346, 350.

Although the hourglass profile of inflated spiral perfusion balloon 230 is illustrated with consecutive windings 340 that have outer diameters which gradually decrease towards waist section 348 in a tapered or continuous manner, the profile may have alternative configurations (not shown) that approximate a barbell shape in which all windings 340 within each section 346, 348, and 350 are of approximately the same diameter. Further, as a non-limiting example, proximal and distal sections 346, 350 may be mirror images of each other as shown in FIG. 5 wherein the outer diameter of windings 340 of proximal section 346 are approximately identical to the outer diameter of windings 340 of distal section 350, but the tapered sequence is reversed. In other examples, although the windings 340 of proximal and distal sections 346, 350 each have greater outer diameters than windings 340 in waist section 348, the windings of proximal section 346 may have greater outer diameters than the windings of distal section 350 or vice versa.

Inner shaft 214 of elongate catheter shaft 211 extends through perfusion lumen 452 of spiral perfusion balloon 230 past a distal end of the balloon. In one embodiment shown in FIG. 7, when spiral perfusion balloon 230 is inflated, inner shaft 214 may extend through perfusion lumen 452 off-center such that it contacts the inner surfaces of at least some of the coiled windings 340. In one embodiment, in addition to tube 336 being anchored to balloon catheter 210 at balloon proximal end 342, the inner surfaces of one or more windings 340 of spiral perfusion balloon 230 may be attached to inner shaft 214. For example, one or more windings of waist section 348 may be secured to inner shaft 214 with a flexible adhesive. In various embodiments, inner shaft 214 may be curved (not shown) to make contact with, and be secured to most or all of windings 340 along the hourglass-shaped balloon 230. Alternatively, hourglass-shaped balloon 230 may be asymmetrically aligned (not shown) such that most or all of the windings 340 make secure contact with inner shaft 214 on a straight line extending through lumen 452 on one side of the balloon.

Figure 8:
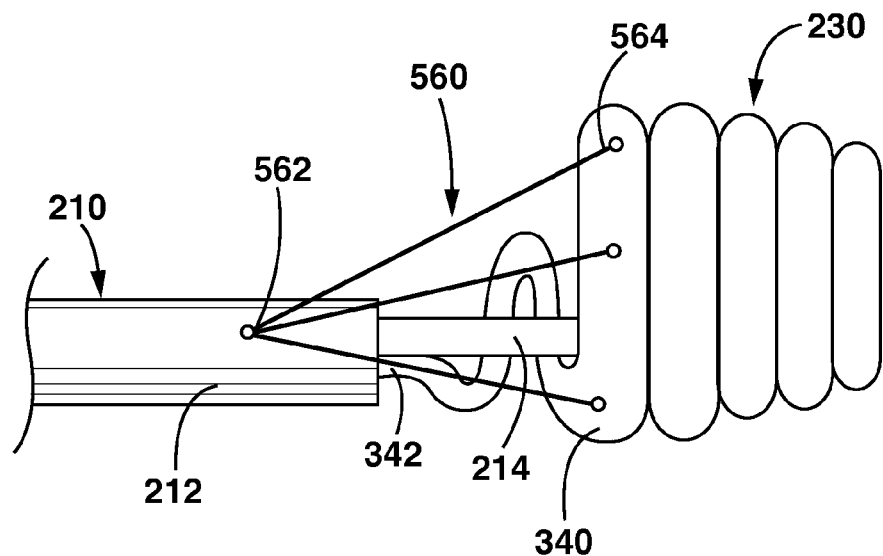
FIG. 8 is an enlarged side view of a proximal portion of a spiral perfusion balloon according to another embodiment hereof, wherein the spiral perfusion balloon includes guide struts on a proximal end thereof.

After spiral perfusion balloon 230 is inflated in situ to dilate the valve, balloon 230 is deflated and balloon catheter 210 is retracted and removed from the patient. FIG. 8 is an enlarged view illustrating a proximalmost portion of spiral perfusion balloon 230 where it is attached to outer shaft 212. In order to reduce the profile of the deflated spiral perfusion balloon 230 so that it can be efficiently removed, one or more guide struts 560 may extend between a proximal winding 340 of spiral perfusion balloon 230 and outer shaft 212 of balloon catheter 210. Guide struts 560 operate to guide or direct spiral perfusion balloon 230 into a guide catheter or sheath (not shown) during retraction of the balloon. Guide struts 560 are sufficiently slender to not compromise blood flow through perfusion lumen 452 when spiral perfusion balloon 230 is inflated. Guide struts 560 may be flexible filaments or tethers formed from a suitable material, including but not limited to polyamide, polyethylene, polyester, ultra high molecular weight polyethylene (UHMWPE), or a high strength suture material. A proximal end 562 of each guide strut 560 is bonded or otherwise affixed to a distal region of outer shaft 212, and a distal end 564 of each guide strut 560 is tied around or otherwise affixed to a proximalmost winding 340 of spiral perfusion balloon 230. In one embodiment, a plurality of guide struts 560 are equally-spaced around the circumference of spiral perfusion balloon 230, and are connected to one or more locations around outer shaft 212.

Figure 9:
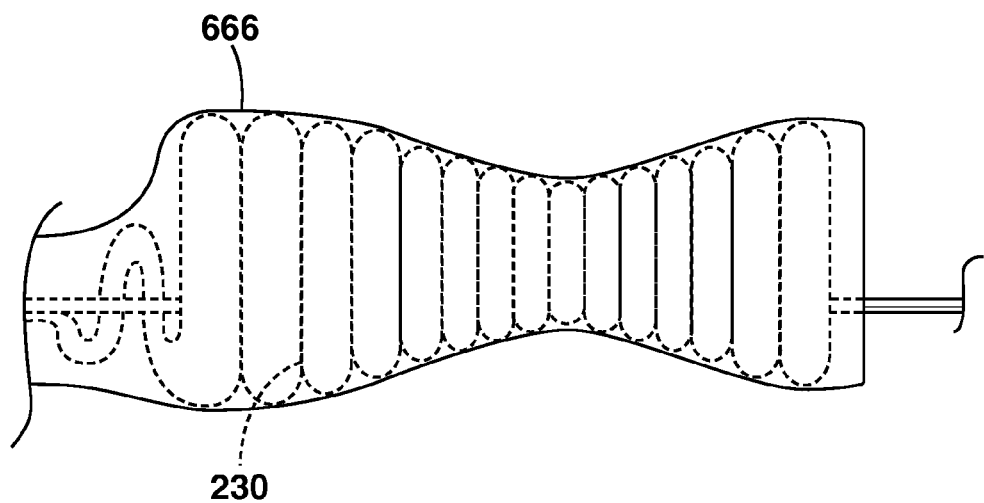
FIG. 9 is an enlarged side view of a spiral perfusion balloon according to another embodiment hereof, wherein an elastomeric sheath surrounds the spiral perfusion balloon.

In addition to or in the alternative, an elastic sheath may be disposed around spiral perfusion balloon 230 and may be utilized to reduce the collapsed profile of deflated spiral perfusion balloon 230 so that it can be more easily inserted or removed from the patient. Referring now to FIG. 9, an elastic sheath 666 may be provided over spiral perfusion balloon 230 before delivery into the vasculature. Elastic sheath 666 will elastically expand with the inflation of spiral perfusion balloon 230 and may be formed of a biocompatible thermoplastic elastomer or viscous forms of natural or synthetic rubber. Preferably, the material is an elastomeric material such as MED 10-6640 two-component silicone rubber by NUSIL, which has a very high elongation before breakage. When spiral perfusion balloon 230 is inflated, sheath 666 will expand without exceeding its elastic limit as shown in FIG. 9. During deflation of spiral perfusion balloon 230, sheath 666 radially contracts and returns to its original shape, thereby urging spiral perfusion balloon 230 back to its initial wrapped profile.

Figure 10:
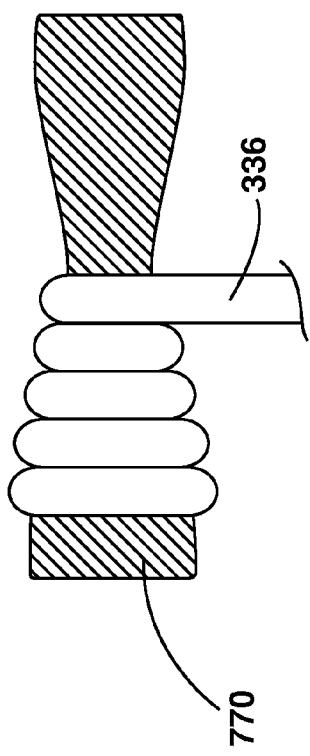
FIGS. 10 and 11 are schematic illustrations of a method of forming a spiral perfusion balloon according to an embodiment hereof.
Figure 11:
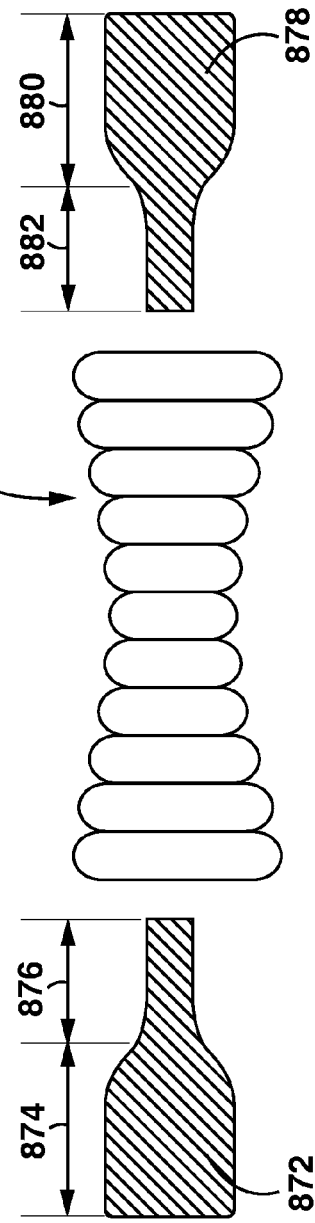

Spiral perfusion balloon 230 may be manufactured in a number of ways. For example, referring to FIGS. 10 and 11, tube 336 may be an elongate, stretch blow-molded cylindrical balloon of suitable diameter that is wrapped onto a mandrel 770 to form the helical configuration of spiral perfusion balloon 230. The shape of mandrel 770 is the intended profile of spiral perfusion balloon 230, i.e., hourglass or barbell shaped, such that the spiral perfusion balloon 230 includes waist section 348 described above. Mandrel 770 is split in the center to allow it to be removed after tube 336 is wrapped and set into the hourglass or barbell profile. More particularly, mandrel 770 includes a first half 872 having an end portion 874 of greater diameter than an interior portion 876 and a second half 878 having an end portion 880 of greater diameter than an interior portion 882. Interior portions 876, 882 of mandrel halves 872, 878, respectively, thus have tapered portions and reduced diameters that abut to form waist section 348 of spiral perfusion balloon 230.

After being wrapped onto mandrel 770, spiral perfusion balloon 230 is pressurized or inflated and adjacent windings 340 of spiral perfusion balloon 230 are heat set in order to ensure that spiral perfusion balloon 230 maintains its shape. For example, heat setting the helical configuration of spiral perfusion balloon 230 may include placing shrink wrap over the balloon, applying heat to fix the balloon in the hourglass or dog-bone shape, and then removing the shrink wrap. In an embodiment, adjacent windings 340 are bonded together with a flexible adhesive, or in the alternative ultrasonic welding or other form of melting material between adjacent windings may be utilized to adhere adjacent windings 340 together. After the helical configuration of spiral perfusion balloon 230 is heat set and bonded, mandrel 770 is split apart and removed as shown FIG. 11, thereby forming perfusion lumen 452 of spiral perfusion balloon 230. Alternatively, an elongate, stretch blow-molded cylindrical balloon of suitable diameter may be wrapped loosely onto a mandrel, and then inserted into a mold having an internal hourglass profile (not shown). End caps can then be placed on the mold and the spiral balloon can be inflated and heat set as described above. While still in the mold, adjacent windings of the spiral balloon may be secured together.

Figure 12:
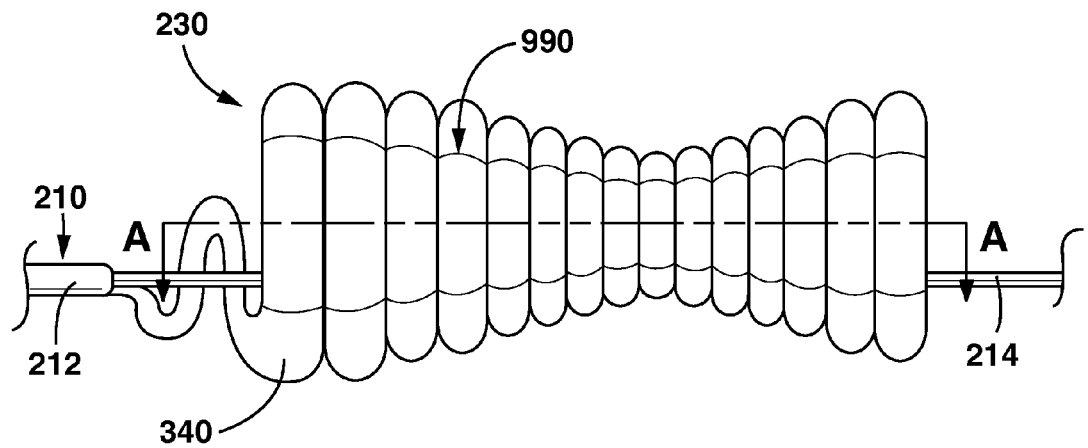
FIG. 12 is an enlarged side view of a spiral perfusion balloon in an expanded configuration according to another embodiment hereof, wherein adjacent windings of the balloon are secured together by a plurality of support weaves.
Figure 13:
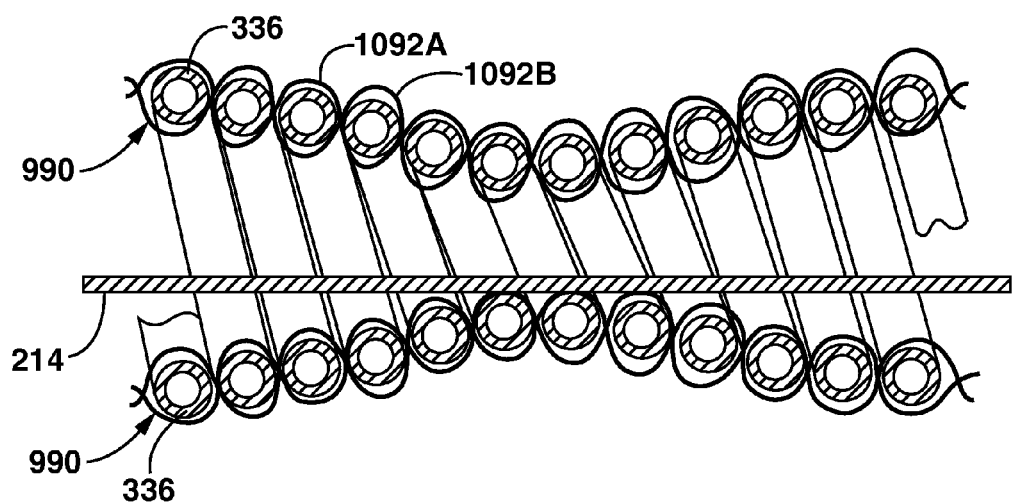
FIG. 13 is a longitudinal sectional view of the spiral perfusion balloon catheter of FIG. 12 taken along line A-A.

Alternatively, adjacent windings 340 may be secured to each other using a support weave 990 shown in FIGS. 12 and 13. Support weave 990 provides axial and radial support to spiral perfusion balloon 230, making it more robust to resist being pulled apart during tracking and inflation. In one embodiment, in order to form a support weave 990, two individual filaments 1092A, 1092B of surgical suture or similar material are longitudinally woven over and then under adjacent windings 340 of spiral perfusion balloon 230, criss-crossing between every pair of adjacent windings and running substantially the entire length of the balloon. In FIG. 13, filaments 1092A, 1092B are shown as being loosely woven around tube 336 only for clarity of illustration. In the inflated configuration shown, filaments 1092A, 1092B would actually be snugly fitted around the windings of tube 336. The ends of individual filaments 1092A, 1092B are secured together adjacent to both the proximal end of the balloon and the distal end of the balloon, and may further be secured to spiral perfusion balloon 230. Alternatively, a single filament of suture material may form support weave 990 by weaving the thread over and then under adjacent windings 340 in a distal direction along the length of the balloon, then "doubling back" in a proximal direction along the length of the balloon, with the single filament thereby criss-crossing itself between all adjacent windings 340 of spiral perfusion balloon 320. Any number of support weaves 990 can be placed around the balloon. For example, multiple support weaves 990 may be equally spaced around the circumference of spiral perfusion balloon 230 as shown in FIG. 12.

Filaments 1092A, 1092B of support weave 990 are formed from a material having sufficient strength to aid in maintaining the stacked coils in the helical configuration of spiral perfusion balloon 230. A selection of suitable filament materials includes but is not limited to polyamide, polyolefin including polypropylene, polyethylene and UHMWPE, polyester, and commercially available non-absorbable, non-metallic monofilament and twisted or braided multifilament high strength suture.

Figure 14:
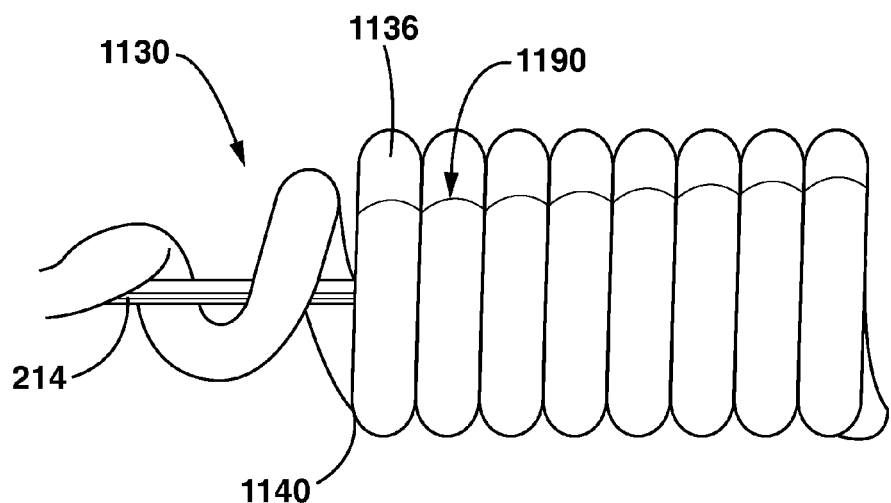
FIG. 14 is an enlarged side view of a substantially cylindrical spiral perfusion balloon in an expanded configuration according to another embodiment hereof, wherein adjacent windings of the balloon are secured together by a plurality of support weaves.
Figure 15:
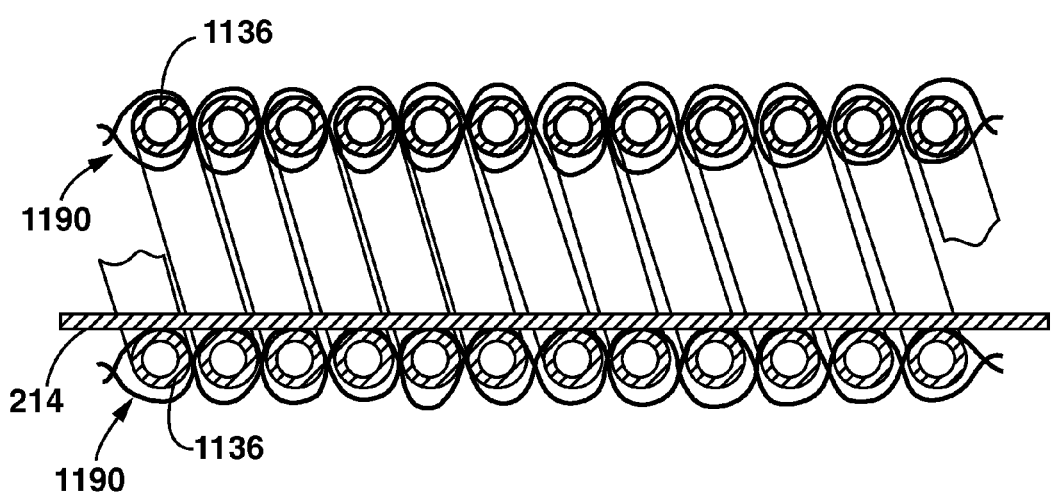
FIG. 15 is a longitudinal sectional view of the spiral perfusion balloon catheter of FIG. 14 taken along line A-A.

Support weave 990 may be applied to spiral or helical perfusion balloons having other configurations besides an hourglass or dog-bone shape. For example, referring now to FIGS. 14-15, multiple support weaves 1190 are shown longitudinally woven between adjacent windings 1140 of a spiral perfusion balloon 1130 having a substantially cylindrical shape or profile, with support weaves 1190 criss-crossing between every adjacent pair of windings and running substantially the entire length of the balloon. In FIG. 15, support weaves 1190 are shown as being loosely woven around tube 1136 only for clarity of illustration. In the inflated configuration shown, support weaves 1190 would actually be snugly fitted around the windings of tube 1136. Spiral perfusion balloon 1130 is formed from a tube 1136 which is similar to tube 336 described above. However, in the inflated configuration, spiral perfusion balloon 1130 does not include a waist or intermediate section of reduced diameter. Rather, adjacent windings 1140 of spiral perfusion balloon 1130 all have substantially the same outer diameter.

In another embodiment, an elastic layer may be applied only to a proximal portion of spiral perfusion balloon 1130, such as a proximal portion of elastic sheath 666 illustrated in FIG. 9. The elastic layer may retard inflation of the surrounded proximal portion of spiral perfusion balloon 1130 such that a distal portion of balloon 1130 located within the ventricle may fully inflate first to anchor the balloon in the heart, and then the remaining proximal portion of the balloon may fully inflate in the aortic valve and the aorta.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment.

What is claimed is:

1. A balloon catheter comprising:
   a catheter shaft having an inflation lumen;
   a perfusion dilatation balloon mounted on a distal portion of the catheter shaft and being formed from an inflatable tube having a balloon inflation lumen extending therethrough and being in fluid communication with the catheter shaft, wherein in the inflated configuration the tube is coiled into a series of contacting windings that together form an hourglass profile wherein inner surfaces of the coiled windings of the inflatable tube define a lumen of the perfusion dilatation balloon to allow blood flow therethrough, wherein in a deflated configuration, the windings of the inflatable tube are radially collapsed to a reduced profile smaller than the hourglass profile and wherein the lumen of the perfusion dilatation balloon is closed to prevent blood flow therethrough; and one or more guide struts that connect a proximal loop of the perfusion dilatation balloon and the catheter shaft and are operable in the deflated configuration to guide the perfusion balloon into a guide catheter.

2. The balloon catheter of claim 1, wherein at least a portion of the catheter shaft extends through the perfusion lumen and distally of the perfusion dilatation balloon.

3. The balloon catheter of claim 2, wherein the catheter shaft is positioned off-center within the perfusion lumen and contacts at least a portion of the inner surface of the coiled windings of the inflatable tube.

4. The balloon catheter of claim 1, further comprising:
an elastic sheath that surrounds the perfusion dilatation balloon and elastically expands upon inflation of the perfusion balloon and returns to its original shape during deflation of the perfusion balloon to aid in reducing a profile of the perfusion balloon for removal.

5. The balloon catheter of claim 1, wherein adjacent windings are bonded together with a flexible adhesive.

6. The balloon catheter of claim 1, wherein adjacent windings are secured to each other by a support weave formed from one or more filaments of material that are woven over and under and criss-crossing between all adjacent windings along substantially the entire length of the balloon.

7. A perfusion dilatation balloon comprising:
an inflatable tube having an inflation lumen extending therethrough, wherein the inflatable tube is wrapped into a series of windings the inner surfaces of which define a perfusion lumen to allow blood flow through the perfusion balloon when in an expanded configuration, and wherein adjacent windings of the inflatable tube are secured to each other with a support weave formed from one or more filaments of surgical suture that are woven over and under and criss-crossing between all adjacent windings along substantially the entire length of the inflatable tube.

8. The perfusion balloon of claim 7, wherein outer diameters of the windings of the inflatable tube are varied to form a perfusion dilatation balloon with an hourglass profile.

9. The perfusion balloon of claim 7, wherein all the windings of the inflatable tube have substantially the same outer diameter to form a perfusion balloon with a cylindrical profile.

10. The perfusion balloon of claim 7, wherein adjacent windings are also bonded together with a flexible adhesive.

11. The perfusion balloon of claim 7, wherein a plurality of support weaves are equally spaced around the circumference of the perfusion dilatation balloon.

* * * * *